United States Patent [19]

Strubbe

[11] Patent Number: 5,046,362

[45] Date of Patent: Sep. 10, 1991

[54] GRAIN LOSS MONITORS FOR HARVESTING MACHINES

[75] Inventor: Gilbert J. I. Strubbe, Zedelgem, Belgium

[73] Assignee: Ford New Holland, Inc., New Holland, Pa.

[21] Appl. No.: 649,639

[22] Filed: Feb. 1, 1991

Related U.S. Application Data

[63] Continuation-in-part of Ser. No. 335,653, Apr. 10, 1989, abandoned.

[30] Foreign Application Priority Data

Apr. 28, 1988 [EP] European Pat. Off. ........... 82200801

[51] Int. Cl.$^5$ .......................................... A01D 75/28
[52] U.S. Cl. ...................................... 73/579; 73/659; 340/684; 340/606; 56/102; 56/DIG. 15
[58] Field of Search ...................... 73/861.24, 579, 584, 73/659, 861, 865.5; 340/684, 606; 56/10.2, DIG 15; 460/4, 5, 6

[56] References Cited

U.S. PATENT DOCUMENTS

| | | | |
|---|---|---|---|
| 3,606,745 | 9/1971 | Girrdat | 460/5 |
| 4,004,289 | 1/1977 | Kirk | 340/267 R |
| 4,036,065 | 7/1977 | Strelioff et al. | 73/432 R |
| 4,149,415 | 4/1979 | Harbour | 73/432 PS |
| 4,337,611 | 7/1982 | Mailander et al. | 56/DIG. 15 |
| 4,360,998 | 11/1982 | Somes | 56/DIG. 15 |
| 4,490,964 | 1/1985 | Eldredge | 56/10.2 |
| 4,825,146 | 4/1989 | Kotyk et al. | 56/DIG. 15 |

FOREIGN PATENT DOCUMENTS

| | | |
|---|---|---|
| 2044266 | 3/1971 | Fed. Rep. of Germany . |
| 2633638 | 2/1977 | Fed. Rep. of Germany . |
| 2632507 | 4/1977 | Fed. Rep. of Germany . |
| 2002903 | 2/1979 | United Kingdom . |
| 2144861 | 3/1985 | United Kingdom . |

Primary Examiner—Hezron E. Williams
Assistant Examiner—Rose M. Finley
Attorney, Agent, or Firm—Larry W. Miller; Frank A. Seemar; Darrell F. Marquette

[57] ABSTRACT

A grain loss monitor for a harvesting machine is provided with detector mechanism including a sensor plate and a transducer associated with the sensor plate. The detector mechanism is disposed for detecting grain loss through the impact of grain kernals on the sensor plate and the transducer has a resonant frequency in the range of 8 to 25 KHz. The grain loss monitor also includes a circuit operable to process the output signals from the transducer.

25 Claims, 6 Drawing Sheets

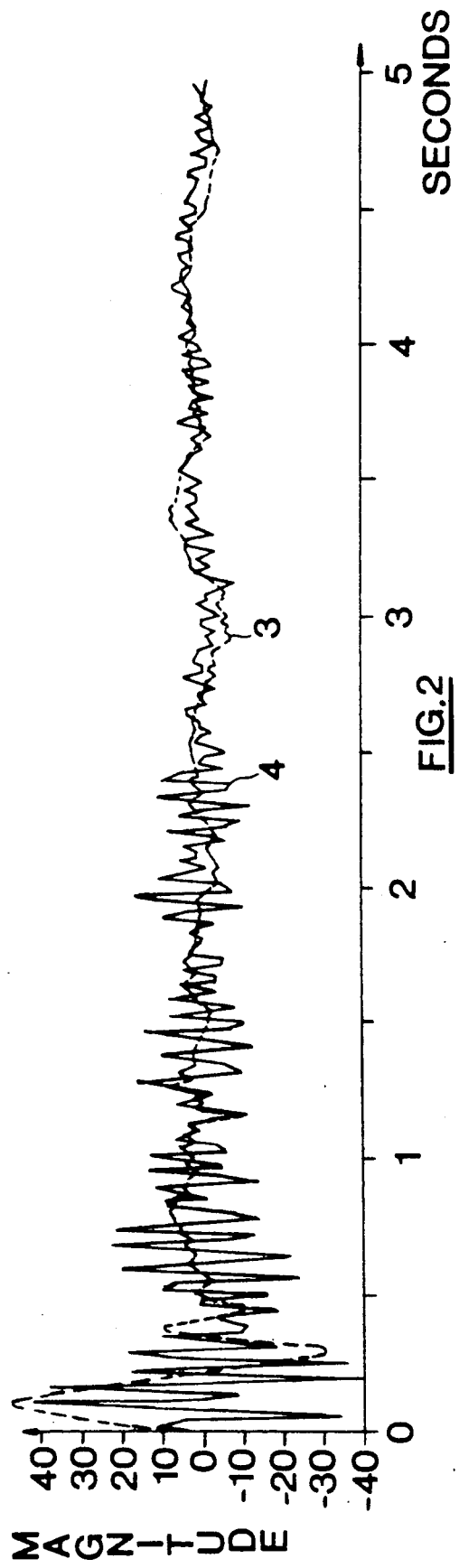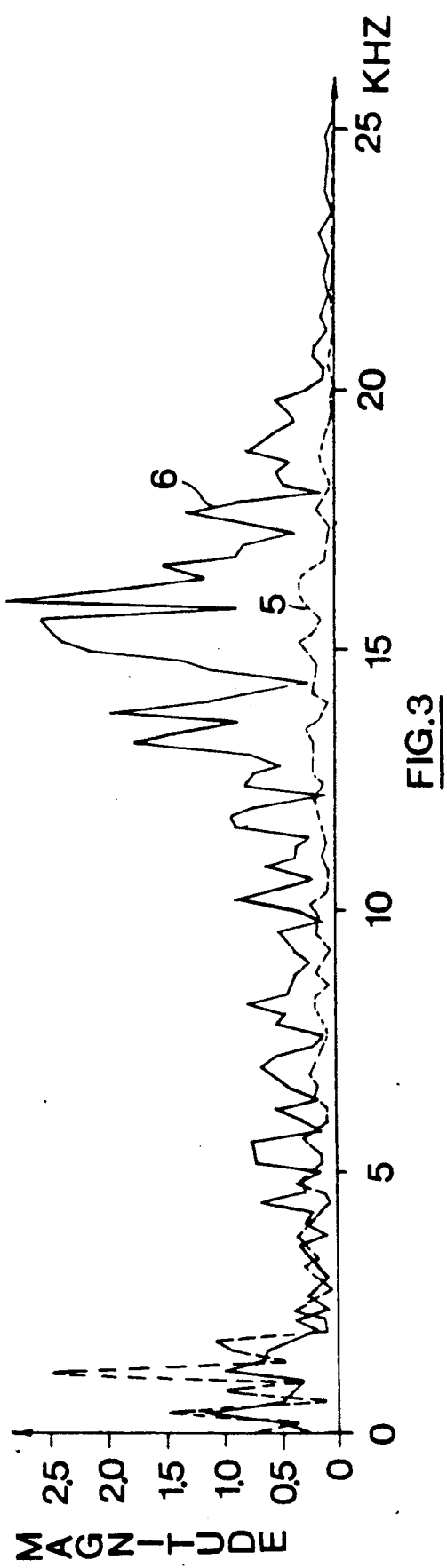

5,046,362

GRAIN LOSS MONITORS FOR HARVESTING MACHINES

CROSS REFERENCE TO RELATED APPLICATIONS

This application is a continuation of U.S. patent application Ser. No. 07/335,653, filed Apr. 10, 1989, now abandoned.

BACKGROUND OF THE INVENTION

This invention relates to an apparatus for measuring grain loss in harvesting machines. More particularly, this apparatus may be used for measuring grain losses occurring at the discharge end of grain handling mechanisms such as the threshing and separating mechanism or the cleaning apparatus of such harvesting machines. Lost grain is that grain which is lost by way of either being entrained in the straw which is discharged from the combine separating mechanism to the ground or by way of being discharged together with chaff and other impurities from the combine cleaning apparatus.

Throughout this specification the reference to "grain" is intended to refer to that part of the crop which is threshed and separated from the discardable part of the crop material which is referred to as "straw". In the following description terms such as "forward", "rearward", "left", "right" etc. are used which are words of convenience and which are not to be construed as limiting terms.

Grain loss monitors for harvesting machines are known in the art and these attempt to monitor the amount of grain which is lost by way of relying on impact detectors which "count" a fraction of the grain which is being discharged at the back of the machine. However, the operator is unable to determine the relative proportion between the fraction of grain which impacts upon the grain loss detector or detectors on the one hand and the total actual losses on the other hand. This gives rise to perhaps the most important problem associated with existing grain loss monitors to the extent that there is not available a monitor which will indicate, in absolute terms, the amount of grain being lost during the harvesting process. Known monitors have only been able to provide some indication which varies more-or-less proportionally with the variations in the magnitude of the actual grain losses.

However, the present invention does not address this particular problem but rather two further problems which equally are associated with known monitors. The first one of these further problems consists of the relatively complicated operation of known grain loss monitors while that the other one is concerned with the lack of accuracy in the measurements in as much as known monitors are unable to distinguish adequately between grain and straw; the latter problem being particularly critical when the crop material is relatively wet.

Regarding the problem of complexity of known grain loss monitors, a plurality of controls require operation by the operator in order to set the monitor for any given circumstance.

For example, there is one control which has to be set according to the type of crop being harvested. This control sets the signal threshold value which must be lower for relatively small grain and which must be higher for relatively large grain. This setting further also is particularly critical in connection with the second problem as will be explained later.

Another control sets the sensitivity of the monitor and should take into account the condition of the crop material being harvested. It may not always be easy to decide whether a crop is wet or dry, for example and, in any event, the conditions can change as the harvesting process progresses so that ideally the monitor settings should be adjusted accordingly.

A third control also has to be operated according to whether a detector being monitored is associated with either the separating mechanism and/or the cleaning sieves of the harvesting machine.

The setting of these controls takes time and experience as, in practice, it requires a relatively complex procedure. In accordance with this procedure, the operator has to calibrate the monitor for each one of the settings of the third control, i.e. the control for selecting between the detectors associated with the separating mechanism and/or the cleaning sieves. As a first step in these calibrating procedures, the operator has to set the first control, i.e. the control of the signal threshold value in accordance with the type of crop material to be harvested. This control should be set sufficiently low so that impacts occasioned by grain kernals on the detector or detectors generate signals in the circuitry associated with these detector or detectors. This thus varies with the specific weight of the grain being harvested.

Next, the operator has to operate the harvester at a capacity rate which he expects to correspond to the grain loss rate which he considers to be just within the acceptable limits. He then sets the second control, i.e. the control for setting the monitor sensitivity so that an appropriate monitor "reading" is generated. Next, he physically checks the straw, chaff and other debris which is being discharged by the machine and he uses his practiced eye to decide whether or not the extent of grain loss that actually occurs is indeed at the rate he has choosen to be acceptable. If it is not, then a further test run is made at a different capacity rate which is expected to entrain the grain loss rate which is acceptable. The second control is reset to generate an appropriate monitor "reading" and the physical checking of the material issuing from the harvester is repeated. These steps are repeated until on the one hand, the maximum capacity rate for a given grain loss rate, which is considered still to be acceptable, is obtained and, on the other hand, the second control is set so as to generate a monitor "reading" which is adequate at this acceptable grain loss rate.

When the operator decides that the grain loss is at the acceptable rate, he then attempts to operate the machine so as to keep the grain loss monitor "reading" at the same value. If the operator does not use his practiced eye to effect this calibration of a know grain loss monitor, then grain loss can be relatively high even when the monitor might indicate otherwise. Also, the opposite may be true in as much as the grain loss monitor possibly could indicate that there is grain loss which, whilst being true, is at a level which is significantly less than is considered to be acceptable. This would unnecessarily curtail the harvester capacity. This calibration is particularly difficult because actual quantification of the grain loss rate by a mere physical control of the material discharged at the back of the harvester is not possible and this is why the practiced eye of the operator is required for the calibration. The complexity of this calibration is also the main reason why the controls of known monitors tend to be left alone by the operator with a result that known grain loss monitors are of little practical use.

Also, even if the controls are operated in a proper manner, the indicated grain loss still suffers from the problem of being inaccurate in that the or each detector cannot always adequately distinguish between impacts from straw as opposed to impacts from grain. This difficulty arises because the stems of a given crop have nodules or knobs along their length and very often stems will break at these nodules. This gives rise to pieces of straw having a nodule at one end. If such a piece of straw impacts a detector with the nodule leading, then it can give rise to a signal somewhat similar to that created by the impact of a grain kernal. Accordingly, the detector counts such impacting pieces of straw as grain kernals and will thus indicate a greater grain loss than is actually occurring with the result that the operator may change the operating conditions to reduce the grain loss to what he decides is an acceptable level and which he may already be achieving. One operating condition which may be changed to this end is the forward speed of the machine which may be reduced and which thus increases the harvesting time with the attendant expense and yet often is unnecessary in as much as actual grain loss may be within the range which is acceptable to the operator.

Discrimination between impacts occasioned by grain kernals and pieces of straw may be obtained in known grain loss monitors by adjusting the first control, i.e. the control for setting the signal threshold value. Ideally, this control should be set so that the monitor records all grain kernal impacts on the one hand and eliminates all straw impacts on the other hand. However, it has been found that, in practice, a monitor "reading" quite often is generated in part by straw impacts and in part by grain kernal impacts. However, it is very difficult, if not totally impossible, for the operator to accurately assess what part of the monitor "reading" is generated by straw impacts and what other part of the monitor "reading" is generated by the grain kernal impacts.

This problem is even further aggravated by the fact that the point of discrimination between grain kernal impacts and straw impacts greatly fluctuates dependent on the crop conditions such as the moisture content of the crop material being harvested. Wet crop conditions require a lower threshold setting than dry crop conditions because of the relative softness of wet grain kernals and pieces of straw. A threshold setting which is acceptable for dry crop conditions, i.e. which adequately discriminates between dry grain kernals and dry pieces of straw may be too high for detecting impacts of wet grain kernals. Also, an acceptable setting for wet crop conditions may read impacts occasioned by pieces of dry straw as grain kernal impacts. As a consequence, it thus is also very difficult for the operator to decide on the threshold setting of the monitor. The foregoing problems further also are complicated by the fact that, on the one hand, in dry crop conditions the straw is much more brittle. This results in much more pieces of straw with a nodule at one end being formed. Accordingly, in dry crop conditions, also a relatively higher proportion of the impacts received on the grain loss detectors are caused by pieces of straw. On the other hand, it also is much more difficult, in wet crop conditions, for grain kernals to be separated from the layer of straw which is discharged at the rear end of the harvester and thus, proportionally, a smaller number of grain kernals impact on the detectors in wet crop conditions even though the grain loss level may be high.

In view of the high cost of a harvesting operation, it is extremely important to maximize the capacity of a given harvesting machine, consistent with achieving a grain loss rate which does not exceed a set limit.

SUMMARY OF THE INVENTION

Accordingly, it is the object of the present invention to provide a grain loss monitor which is simple to operate and which provides an indication of the magnitude of the actual grain losses occurring which is less distorted by impacts on the detector or detectors by material other than grain than is the case with monitors which are know to date.

According to the present invention there is provided a grain loss monitor for a harvesting machine having detector means including a sensor plate and transducer means associated with the sensor plate, the detector means being disposed for detecting grain loss through the impact of grain kernals on the sensor plate and the transducer means having a resonant frequency. The grain loss monitor also having circuit means operable to process the output signals from the transducer means which has a resonant frequency in the range of 8 to 25 KHz, preferably around 15 KHz.

The selection of the resonant frequency range of the detector means is the result of a very detailed investigation into the signals which are transmitted through a sensor plate when the latter is impacted by an article such as a piece of straw or grain. It has been found that a wave transmitted through a sensor plate as a result of an impact thereon has a high frequency wave front followed by a low frequency wave body; this wave body being determined by the modular behaviour of the sensor plate. Using a Fourier analysis of the wave forms of the signals induced in a detector plate by grain (both dry and wet) and straw (with nodules) impacts on said plate, it was discovered that the high frequency wave fronts of grain kernal impact signals and straw impact signals have different frequencies; the straw impact signals having lower frequency wave fronts than the grain kernal impact signals.

Accordingly, it was then possible to determine a range of resonant frequencies to which the detector means and the associated circuity could be tuned and which resulted in the impacts by grain being "counted" to the general exclusion of the impacts by straw. In this respect, impacts by wet grain are "counted" as well as impacts by dry grain.

The transducer means may comprise either a single transducer or a plurality of transducers which preferably are of the ceramic crystal transducer type. The selection of a ceramic crystal for the transducer gives rise to a number of advantages. This is because, in order to realize sufficient selectivity and, at the same time, have acceptable sensitivity, it is advantageous if the characteristic function of the detector contributes to the signal conditioning. A normal microphone has a flat frequency curve or response and a comparatively low signal output with a high impedance input. This characteristic is not selective enough, at least for the purposes of grain loss monitoring. Moreover, the construction of a normal microphone equally is not robust enough for use on a vibrating assembly such as a combine harvester.

However, the frequency characteristic of a ceramic crystal demonstrates a resonant frequency which is useful in the signal processing. A ceramic crystal behaves as a resonant circuit and amplifies the signal frequencies within its resonant zone. In contrast with vibration instrumentation, wherein the resonant zone of the pick-up is avoided for equal frequency sensitivity, the frequency characteristic of a ceramic crystal is used in a preferred embodiment of the present invention to realise a selective output. The crystal receives the impact signals, by way of physical vibrations, from the detector plate to which it is attached and converts it into electrical output signals in which the frequencies in the resonant zone of the crystal dominate. Accordingly, the use of a ceramic crystal transducer or transducers is particularly useful in realizing the basic inventive concept of selecting a resonant frequency of the detector in the range of 8 to 25 KHz.

The circuit means preferably also includes a high pass filter to which the output of the transducer means is connected. The high pass filter has a frequency domain which is tuned to the resonant frequency of the transducer means on the one hand and to the frequency range of the wave fronts of the signals induced in the transducer means by grain kernal impacts on the detector plate of the detector means on the other hand. This filter preferably is of at least the sixth order and has a steep gradient in the frequency range of 10 to 15 KHz.

BRIEF DESCRIPTION OF THE DRAWINGS

A grain loss monitor in accordance with the present invention will now be described in greater detail, by way of example, with reference to the accompanying drawings, wherein:

FIG. 2 is a time domain graph illustrating vibrations induced on an impact detector;

FIG. 3 is a graph similar to the graph of FIG. 1 and illustrating the output signal from the transducer;

DETAILED DESCRIPTION OF THE PREFERRED EMBODIMENT

Figure 1:
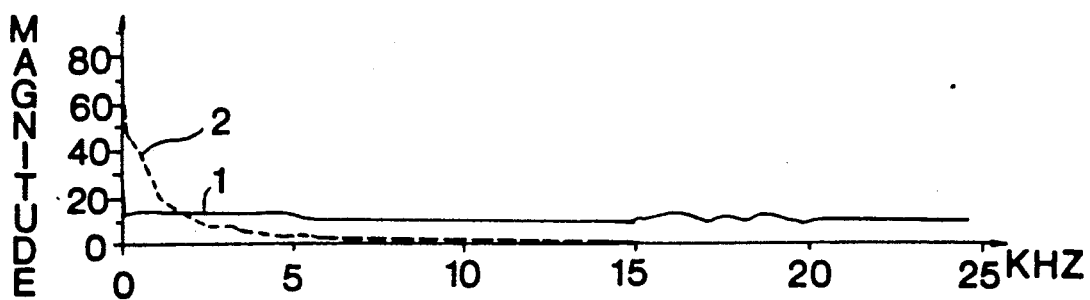
FIG. 1 is a graph illustrating curves obtained from a Fourier analysis of the signals induced in an impact detector.

Turning now to FIG. 1 of the drawings, this illustrates two curves obtained from a Fourier analysis of the signals induced in an impact detector by the impacts of a wheat kernal and a piece of wheat straw with a nodule at one end when dropped from a predetermined height on said detector. FIG. 1 shows a general magnitude scale on the ordinate axis and frequency in hertz along the abscissa axis. The full line curve 1 is that which is obtained by dropping a wheat kernal having an 11% moisture content from a height of 10 cm above the detector plate having associated therewith a transducer or load cell having a wide and constant frequency range. The broken line curve 2 was obtained by dropping a wheat stem (straw) having a nodule at one end, with the nodule leading from the same height on the same detector arrangement. Curve 1 shows that the magnitude of the signal obtained by the impact of a wheat kernal is relatively constant up to at least 25 KHz. However, the signal generated by the straw is of relatively large magnitude initially up to about 5 KHz and then drops dramatically so that in the 15 KHz region, there is virtually no signal level.

The fact that the straw signal 2 greatly exceeds the grain kernal signal 1 in the low frequency range is no surprise in as much as the weight of the piece of straw with the nodule also greatly exceeds the weight of the grain kernal. These findings also indicate that a grain loss sensor tuned in the low frequency zone would mainly record straw impacts rather than grain impacts. This is not at all acceptable. If in contrast therewith the curves 1 and 2 are compared at the 15 KHz point, for example, it will be seen that the signal level of the straw impacts can be ignored as against the signal level of the wheat kernals which is of the order of magnitude 10. The absolute magnitude of the two signals is of no importance; the essential point being that the ratio of the grain kernal signal to the straw signal is high in a given frequency range whereby it is possible to take out the low level signals and hence concentrate on the high level signals.

Figure 4:
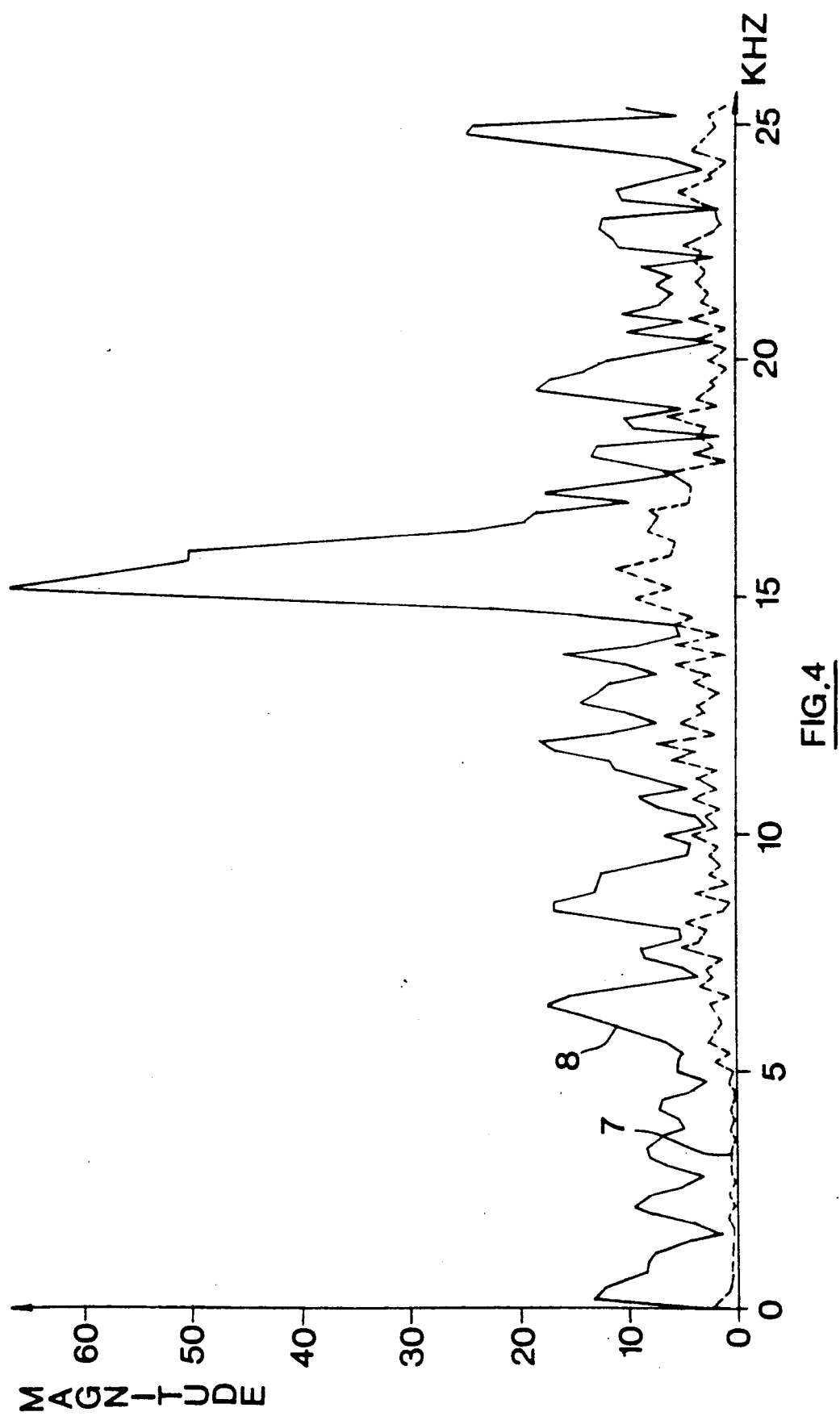
FIG. 4 is a graph similar to the graph of FIG. 4 and illustrating the output signal after being passed through the high pass filter.

Turning now to FIGS. 2-4, these curves were obtained using a detector in the form of a plate having attached thereto a crystal detector having a resonant frequency in the range of 15 KHz. This thus is in contrast with the arrangement from which the signals of FIG. 1 are derived, this arrangement having a detector with a load cell having a wide and constant frequency range. FIG. 2 is a time domain graph with magnitude plotted against time in seconds. The broken line curve 3 resulted from the impact of straw and the full line curve 4 resulted from the impact of a wheat kernal on the detector. From a comparison of the curves 3 and 4 of FIG. 2 it will be seen that no useful information can be derived therefrom for measuring grain losses in as much as both curves substantially overlap each other. However, FIG. 2 nevertheless is useful in as much as it tends to confirm the findings that can be derived from FIG. 1 and following which, on the one hand, a grain kernal impact generates a signal wherein the high frequency vibrations proportionally are relatively important and, on the other hand, a straw impact generates a signal wherein the low frequency vibrations proportionally also are relatively important.

FIG. 3 shows a graph similar to FIG. 1 in as much as a general magnitude scale on the ordinate axis and a frequency scale in hertz along the abscissa axis are shown. Again, the broken line curve 5 shows the straw impact signal while that the full line curve 6 illustrates the grain kernal impact signal. From these curves it will be seen that at around the 15 KHz point, there is a signal level in excess of 2.5 generated by the wheat kernal, whereas the straw generated signal level is of the order of 0.4. Therefore, the ratio of these signals at 15 KHz is significantly high. In other words, the signal amplitude of the grain kernal signal is high in the high frequency range while that in that same frequency range the amplitude of the straw signal is low. This graph also confirms that in the low frequency range the amplitude of the straw signal substantially exceeds the grain kernal signal.

Figure 8:
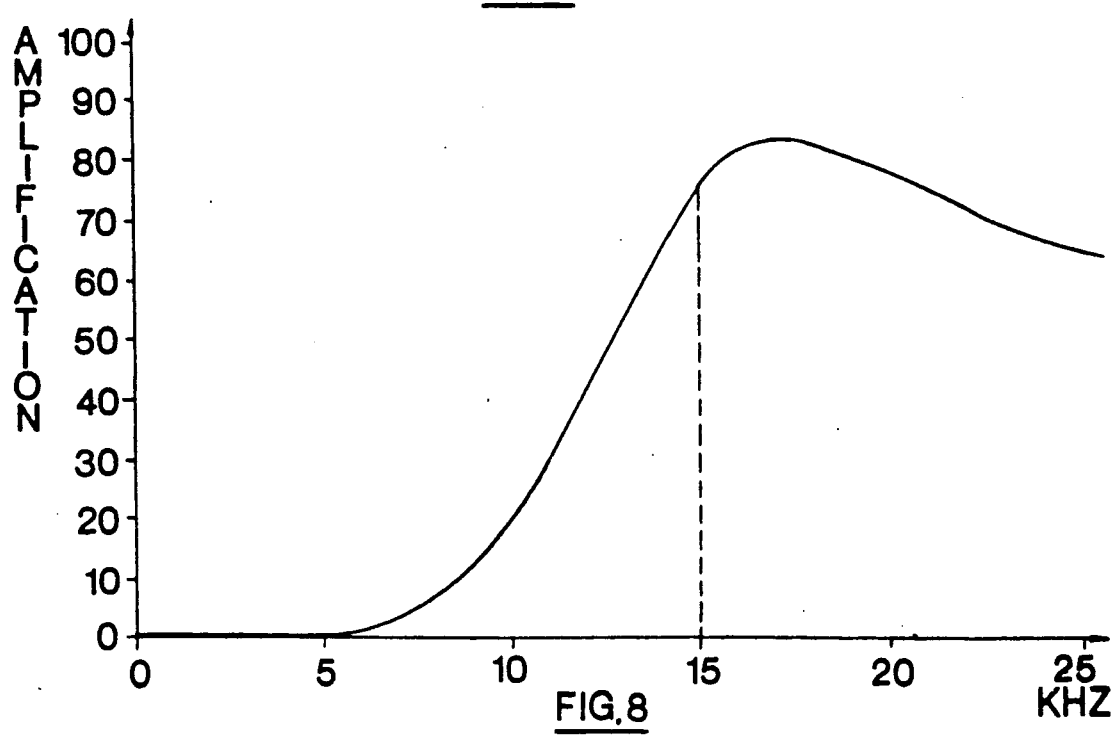
FIG. 8 is a graph illustrating the characteristics of the preferred high pass filter.

FIG. 4 is very similar to FIG. 3, except that it shows the results of a Fourier analysis on the signals of FIG. 2 after they have been passed through a high pass filter, the characteristics of which are illustrated in FIG. 8. Again, the broken line curve 7 illustrates the signal obtained from the impacting straw (nodule leading) and the solid line curve 8 shows the signal resulting from the impact of the wheat kernal. FIG. 4 shows that the magnitude of the signal generated by the impacting wheat kernal peaks significantly at around 15 KHz and has a magnitude in excess of 60 whereas the signal generated by the impacting straw is of a more consistent level of magnitude. Thus, it will be seen that, at the 15 KHz point, the ratio of the magnitudes of the wheat kernal and straw signals is relatively high which is consistent with the curves of FIG. 3.

The high pass filter used for filtering the signals preferably is of at least the sixth order so as to obtain a relatively steep gradient in the selected frequency range; this range being situated between 10 and 15 KHz in the arrangement of which the characteristics are illustrated in FIG. 8. This high pass filter is preferably constructed to incorporate an operational amplifier, such as is found in the design of an RC active filter, so that the high pass filter can both filter and amplify a signal. The graph of FIG. 8 plots the amplification factor of the filter on the ordinate axis against the frequency levels on the abscissa axis and, as a matter of fact, FIG. 4 may be considered as being the result of the multiplication of the signals of FIG. 3 with the amplification factors illustrated in FIG. 8.

It has been found that with the use of a high pass filter of the type as described above, mainly only the wave fronts of the grain kernal impact signals are considered in as much as these wave fronts have a high frequency whereby they pass through the filter and are amplified. In contrast therewith the remainder of the grain kernal impact signals have a lower frequency whereby they are filtered out. In as much as the straw impact signals altogether have a much lower frequency (even also the wave fronts thereof), these signals equally are filtered out to a substantial degree. In summary, the use of a high pass filter of the type as described has made it possible to look mainly at the wave fronts of the grain kernal impact signals while ignoring to a great extent the rest of these signals as well as the entire straw impact signals.

Figure 5:
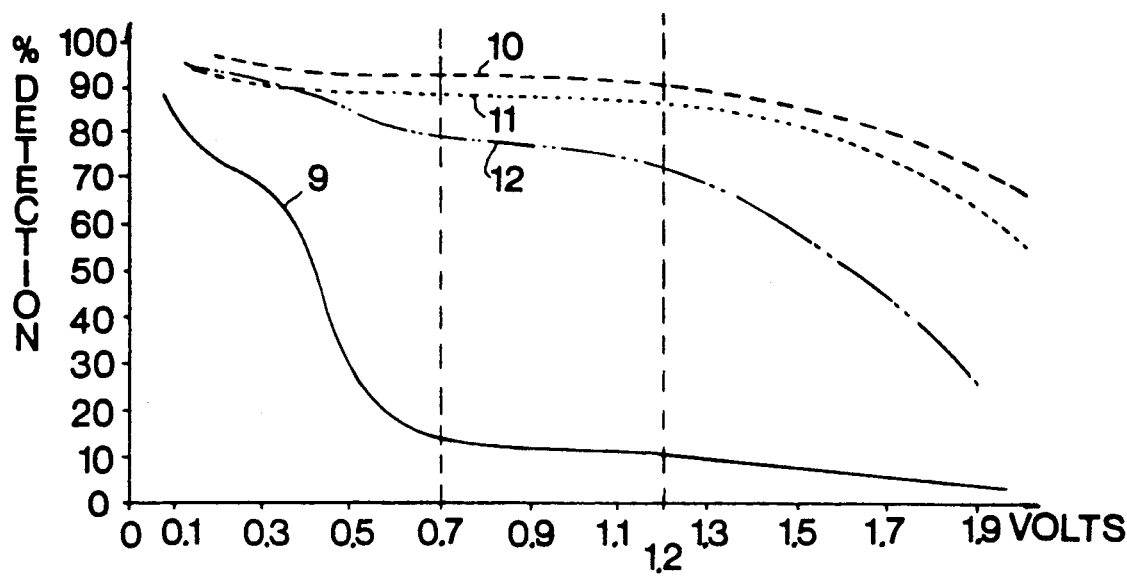
FIG. 5 is a graph illustrating the results of a study conducted to determine the discrimination rate of wheat kernels and straw.

Turning now to FIG. 5, this figure summarizes the results of one aspect of the study which has taken place and illustrated in its various aspects in FIGS. 1 to 4 of the drawings. More specifically it illustrates the ability to discriminate between grain and straw in a given condition. It shows the detection rate or percentage detection (ordinate axis) of impacts of wheat kernals and straw against threshold voltages (abscissa axis) with a grain loss monitor having an impact detector of the type including a crystal transducer with a resonant frequency of 15 KHz on the one hand and also having high pass filter of at least the sixth order on the other hand.

By percentage detection or detection rate is meant the proportion of signals recorded by the monitor when set at any given threshold voltage. As an example, an 80% detection rate at a threshold voltage of 1 volt means that, with the monitor set at a threshold voltage of 1 volt, the monitor responds to and records 80 impacts out of a total number of 100 impacts that occurred on the impact detector. This also implies that 20 impacts thereof are ignored by the monitor. In other words, 80 impacts out of 100 impacts on the given impact detector are translated into signals of at least 1 volt.

For putting together the graph of FIG. 5, the threshold voltage for the signals generated at the detector by impacting wheat kernals and straw was varied between 0.1 and 2 volts to establish whether threshold values per se would distinguish clearly grain signals from straw signals. Also, the length of the detector plate of the impact detector was varied to check the possible influence of this variable. Four curves are shown in FIG. 5 which represent:

Curve 9: The detection rate of the impacts by pieces of straw from wheat crop material dropped from a height of 100 mm on a detector plate with a length of 265 mm and using a single crystal transducer; said pieces of straw having nodules by which the pieces of straw impacted upon the detector plate.

Curve 10: The detection rate of the impacts by wheat kernals dropped from a height of 100 mm on a detector plate with a length of 265 mm and using a single crystal transducer.

Curves 11 and 12: The same as curve 10 except that the detector plate has a length of 850 mm and 1400 mm, respectively.

Curve 9 shows that, for a low threshold value, the percentage detection of straw impacts is relatively high at about 75%. This also indicates that with a monitor set at a low threshold value (below 0.5 volts) the monitor "reading" will very much be influenced by the amount of straw impacting upon the detector surface. This, of course, is not acceptable. However, the detection rate of straw impacts dramatically falls from a threshold voltage of 0.3 volts onwards and is less than 20% with a threshold voltage set at 0.7 volts or higher. Considering the threshold voltage range between 0.7 volts and 1.2 volts, the detection rate of straw impacts appears to be relatively constant at about 12%, which is considered to be acceptable.

From curve 10 it will be seen that the percentage detection of grain impacts with the same detector arrangement as for curve 9 is of the order of 95% with threshold voltages in the range of 0.7 to 1.2 volts so that, if this threshold range is employed, the detection of grain will predominate.

From a comparison of the curves 10, 11 and 12 it also will be seen that the detection rate is substantially independent of the width of the detector plate in spite of only employing one transducer per impact detector. Indeed, while it is seen that the detection rate for the longest (widest) detector investigated (curve 12) is of the order of 80% (as opposed to 95% for the shortest detector) in the voltage threshold range of 0.7 to 1.2 volts, this is still significantly higher than the 12% straw detection rate in the same voltage threshold range. This 80% detection rate still gives an adequate result against the 12% detection rate of straw in the same range.

The foregoing analysis thus tends to indicate that it must be possible to build a grain loss monitor which, for a given condition, discriminates up to a satisfactory level between grain and straw. To this end, it is necessary to provide a monitor including on the one hand an impact detector having a crystal detector with a resonant frequency in the range of 15 KHz and on the other hand a high pass filter which is tuned to this frequency domain. However, the monitor also should be able to discriminate between grain and straw in a wide range of conditions.

So far the influences of varying crops and crop conditions have not been considered. However, this now will be addressed hereafter with reference to FIG. 6 which charts the percentage detection of different types of crop (grain) and straw. The detection point on the detector used to generate these charts was 150 mm to one side of the single crystal detector employed and which had a resonant frequency of the order of 15 KHz. The conditioning circuit employed was with a sixth order filter and set at a threshold of 1 volt. In other words, the threshold setting of the monitor did not change throughout the comparison test.

In this respect it should be noted that with grain loss monitors known to date, it always has been necessary to adjust the threshold setting when switching from one crop or crop condition to a very different crop or crop condition. Indeed, when, for example, the monitor is set for operation in wheat and oats were harvested, then, because of the differences in the crop characteristics (oats being very much softer than wheat) the monitor would not record any oats kernal impacts. Accordingly, this tended to indicate that there was no grain loss even though a substantial grain loss actually could occur. Similarly, if the monitor was set for operating in oats and if wheat was harvested, the monitor responded very much to wheat straw impacts in addition to the wheat kernal impacts. As a consequence the monitor threshold setting had to be adjusted in accordance with the crop being harvested.

Figure 6:
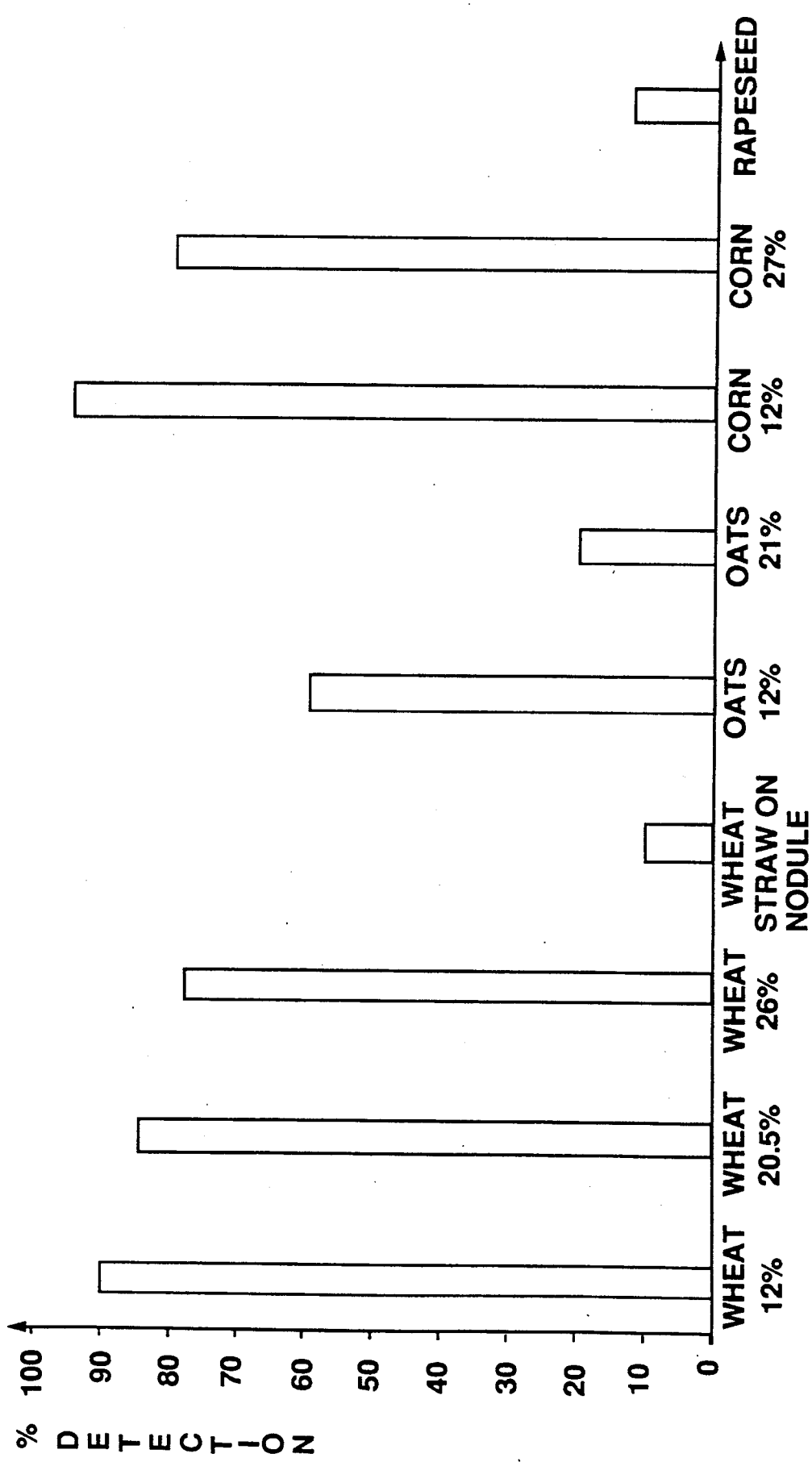
FIG. 6 is a diagram illustrating the detection rates, using the present invention, of various types of grain and straw.

Considering FIG. 6 more closely it will be seen that the detection rates in four different crops, namely wheat, oats, corn and rape seed have been compared. This small range of crop may be considered to be representative of the wide variety of crops that may be harvested with combine harvesters. Furthermore, FIG. 6 also compares the detection rates in different crop conditions.

Considering first the four columns on the left hand side of FIG. 6, it will be noted that the humidity has only a minimal influence on the detection rate of wheat grain in as much as this detection rate is around 90% for relatively dry wheat (12% moisture content) and is still around 80% for wet wheat (26% moisture content). This compares very favourably with the roughly 12% detection rate of dry wheat straw; the detection rate of humid wheat straw still being smaller. Apart from these findings, it should be remarked that a reduction of the grain detection rate associated with an increase in the moisture content does not come as a surprise in as much as an increased moisture content softens the grain kernals. However, the essential finding is that, even in the worst condition, there still is a wide gap between the detection rates of wheat kernals and straw without having to adjust the threshold value to the particular condition and whereby a reliable signal is obtained. As a matter of fact, wheat probably is one of the most difficult crops to accurately discriminate between the grain kernals and straw in as much as the physical characteristics of the nodules come rather close to the physical characteristics of wheat kernals, especially when humid wheat kernals are compared with dry nodules.

Considering next the two columns representing the detection rates of oats kernals, it will be remarked that, without adjustment of the threshold value of the monitor, this detection rate is still around 60% for dry oats (12% moisture content) and drops to about 20% for wet oats (21% moisture content). This is considered to be a remarkable accomplishment even though these detections rates are substantially lower than the detection rates for wheat in as much as known monitors had a zero detection rate of oats kernals if the threshold value was not readjusted to the type of the crop. Furthermore, and although the detection rate of oats straw has not been shown in FIG. 6, it should be remarked that, because of its physical characteristics, oats straw is not detected with the monitor setting as described above.

Accordingly, there is absolutely no problem with the discrimination between oats kernals and oats straw. The foregoing findings also indicate that, on the one hand, the threshold adjustment can be dispensed with when switching from wheat to oats and, on the other hand, the drop in grain kernal detection rates when switching from wheat to oats can be compensated by adjusting the sensitivity setting of the monitor. Also, the substantial drop in the detection rates when switching from dry oats to wet oats can be compensated in this manner; the essential point being that no threshold adjustment is necessary.

Turning now to the columns indicating the detection rates of dry and wet corn (12% respectively 27% moisture content), these detection rates are found always to be situated above 80%. Corn stalks and corn trash such as pieces of corn cobs are not detected with the monitor according to the invention and set as described above.

Turning now finally to the column indicating the detection of rapeseed, it is quite remarkable and surprising that, without any threshold adjustment, the monitor still has a detection rate of about 15% of the relatively small rapeseed kernals.

In summary, the exercise as described above has indicated that the grain loss monitor according to the invention and as described above, i.e. a grain loss monitor including a high pass filter and an impact detector having a detector plate with a crystal transducer with a resonant frequency in the range of 15 KHz associated therewith, will adequately distinguish between grain and straw impacts in a wide variety of crops and crop conditions without having to adjust the threshold value to these crops and crop conditions; the only adjustment still being necessary being the sensitivity adjustment. This sensitivity adjustment still necessitates a calibration of the monitor involving a physical checking of the actual losses at the rear of the harvester. To this end, the monitor is provided with a single control means and this has greatly simplified the setting procedure.

Figure 7:
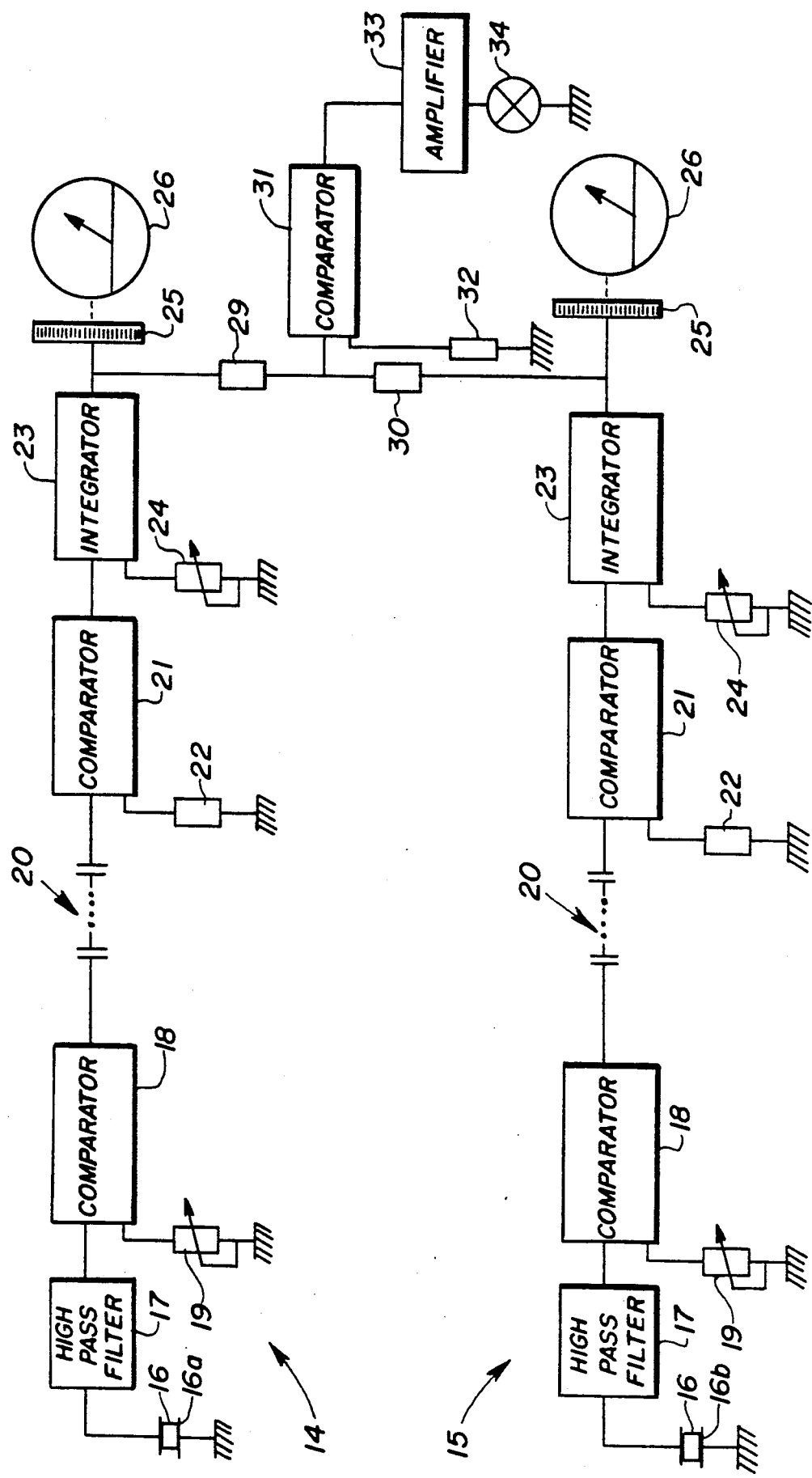
FIG. 7 is a block diagram of a grain loss monitor in accordance with the present invention.
Figure 9:
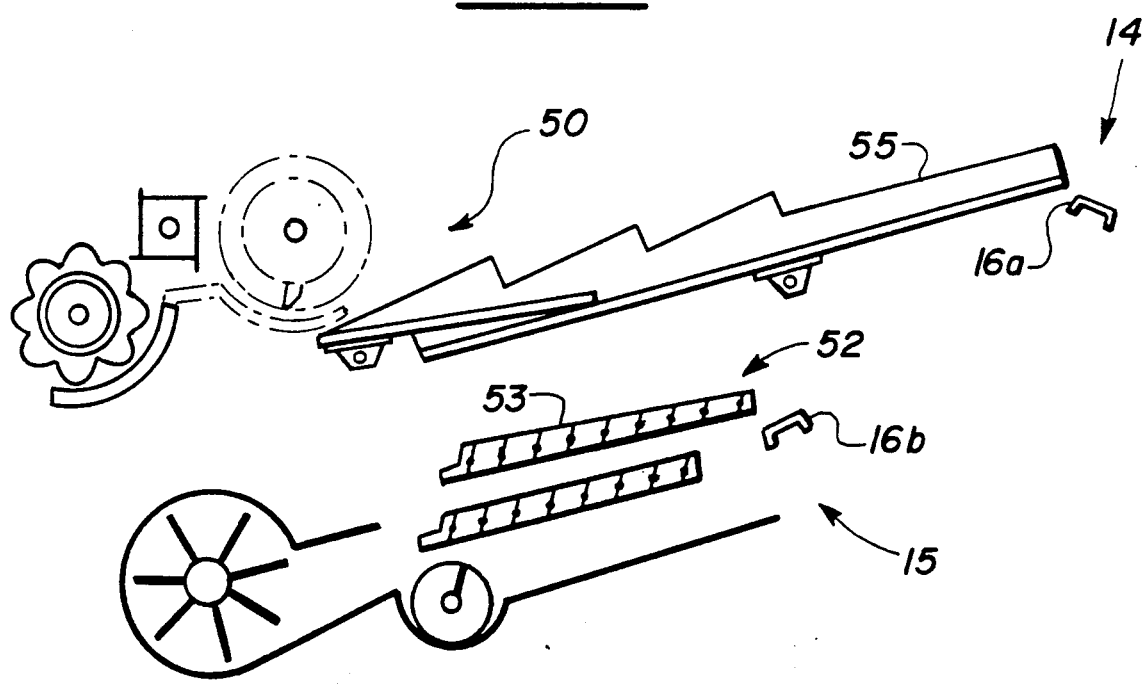
FIG. 9 is a schematic side elevational view of a conventional harvesting apparatus utilized in a combine harvester.

Turning now to FIG. 7 of the drawings, this shows a block circuit diagram of a grain loss monitor constructed in accordance with the present invention. FIG. 9 schematically depicts a conventional combine harvesting apparatus in which the instant grain loss monitor could be utilized. Referring now to FIGS. 7 and 9, it can be seen that the circuit comprises two channels 14 and 15, channel 14 being for a detector 16 or detectors forming part of a sensor plate 16a situated at the discharge end of the separating mechanism 50 and the other channel 15 being for a detector 16 or detectors forming a part of the sensor plate 16b located at the discharge end of the upper sieve 53 of the cleaning mechanism 52 of a combine harvester. The detectors are situated so that a fraction of the grain entrained with the straw, chaff and other debris discharged at the rear of the machine and which is separated from said straw, chaff and other debris, is caused to impact on said detectors. In case of a conventional combine harvester, as depicted in FIG. 9 the detector 16 or detectors associated with the separating mechanism 50 usually are mounted on one or more straw walkers 55 at positions adjacent to and rearward of and slightly below the discharge ends thereof. In case of rotary combine harvesters (not shown) which do not employ straw walkers, the detector or detectors preferably are positioned beneath the rear end portion or end portions of the separating concaves.

The detectors 16 used in the channels 14 and 15 are not illustrated in the drawings but may be in the form of stainless steel plates to which crystal transducers are connected and such as disclosed in the co-pending U.S. patent application Ser. No. 335,620, granted as U.S. Pat. No. 4,933,589 on June 12, 1990, and entitled "Impact Detectors." The descriptive portions of this co-pending application are hereby incorporated herein by reference.

Each detector plate has associated therewith a single ceramic crystal transducer 16 having a resonant frequency in the range of 8 to 25 KHz. Preferably this resonant frequency is in the range of 12 to 25 KHz. Very good results have been obtained with a crystal having a resonant frequency in the range of 15 KHz. Even better results have been obtained with an impact detector having twin ceramic crystal transducers provided in a single transducer housing associated with the detector plate. In this twin transducer arrangement, the crystal transducers had a resonant frequency of 11.6 KHz, respectively 19.5 KHz. In other words, the respective resonant frequencies were situated at the opposite ends of the selected range.

The output of the crystal 16 for each of the channels 14 and 15 is applied to high pass filter 17 and the output of the latter is applied to a first comparator 18 with which is associated a variable threshold device 19. The output of the first comparator 18 is applied to a second comparator 21 having a fixed threshold device 22 associated therewith and which is provided to eliminate any noise on the relatively long lead 20 which connects the comparator 18 with the comparator 21, the former being physically located on the detector plate and the latter being located in the cab of the combine harvester (not shown). The output of the comparator 21 is applied to an integrator 23 which has an adjustable gain control 24 associated therewith. The output of the integrator 23 is applied either to a bank of light emitting diodes (LED's) 25 and/or a meter 26. The amplitude level of the signal at the output of the integrator 23 dictates how many of the LED's 25 are illuminated or energised, thus giving an indication of the grain loss which is being monitored. Similarly, the extent of movement of the needle of the meter 26, when employed provides a similar indication.

The high pass filter 17 in each of the channels 14 and 15 is tuned to the crystal transducer 16 to which it is associated and is of the type having a relatively steep gradient between 10 and 15 KHz. In order to achieve these characteristics, preferably a filter of at least the sixth order is employed. As noted above, this high pass filter 17 is constructed so as to incorporate an operational amplifier so as to provide the functions of both filtering and amplifying the signal, such as is found in an RC active filter. The characteristic curve of this high pass filter is shown in FIG. 8 and it will be seen that, below the 5 KHz a signal is not amplified. In contrast therewith an amplification factor in the range of 70 to 80 is applied to signals in the range above 15 KHz.

It would also be possible to use a band pass filter tuned to the resonant frequency of the crystal transducer 16. However, it is not always easy to ensure that the correct band pass is obtained and this is why a high pass filter as described is preferred.

The use of the high pass filter 17 has made it possible to basically look at the wave fronts of the grain kernal impact signals only which have a frequency which is higher than the frequencies of as well the rest of the grain kernal impact signals as the entire straw impact signals and which thus basically are ignored. This is an important reason why the monitor according to the invention is able to adequately discriminate between grain and straw without having to reset the monitor each time the crop and crop conditions vary.

It should also be noted that the adjustable threshold device 19 for the comparator 18 is set at the factory on manufacture and may be dispersed with. The only control of the grain loss monitor which has to be effected by the operator is that of the gain control 23 which is necessary in order to obtain a signal of a sufficient level (sensitivity) to drive the LED's 25 or the meter 26 for all the crops and crop conditions.

While that the threshold device 22 associated with the second comparator 21 has been shown and described as being fixed, this threshold device 22 nevertheless also may be made adjustable to permit a setting for eliminating all of the noise on the lead 20 which may be different from one machine to another. However, this type of adjustement is not normally done by the operator. Instead it may be done by the manufacturer and/or the dealer. Anyway, this type of adjustment has nothing to do with the adaptation of the monitor to the crop and condition of the crop being harvested.

The fact that each crystal 16 and the processing circuitry associated therewith, especially the high pass filter 17, are tuned to a frequency in the range of 8 to 25 KHz (preferably 12 to 25 KHz, ideally 15 KHz) means that essentially only the impacts by grain on the or each detector are sensed and impacts by straw (even with leading nodules) are ignored systematically, without the operator having to adjust the threshold value of the monitor to adapt the monitor to the crop and crop condition. Thus, the grain loss monitor constructed in accordance with the present invention is far more accurate than known monitors and represents a very significant advance in the art.

To appreciate the importance of the progress the art provided by the invention, it may be useful to consider the following comparison which has been made between the monitor according to the invention on the one hand and various grain loss monitors available on the market on the other hand. The setting of the several monitors has not been readjusted during the entire comparison.

|  | Invention | A | B | C | D |
|---|---|---|---|---|---|
| resonant freq. of transducer | 15 KHz | 2.5 KHz | 6 KHz | 6 KHz | higher than 100 KHZ |
| Conditioning circuit | High pass 6th order | Conventional amplifier | Low pass 1st order | Loss pass 3rd order | High pass 4th order |

-continued

|  | Invention | A | B | C | D |
| --- | --- | --- | --- | --- | --- |
| Conditioning circuit | 16 KHz | higher than 25 KHz | 1.5 KHz | 0.5 KHz | 25 KHz |
| [1] detection rate wheat at 12% moisture | 90% | 70% | 65% | 95% | 60% |
| [2] detection rate wheat straw nodule leading at 12% moisture | 12% | 88% | 80% | 40% | 40% |
| [3] detection rate wheat at 26% moisture | 78% | 63% | 57% | 84% | 30% |
| ratio [1]/[2] | 7.5 | 0.8 | 0.8 | 2.4 | 1.5 |
| ratio [3]/[2] | 6.5 | 0.71 | 0.71 | 2.1 | 0.75 |

It will be remarked from the foregoing comparison that most prior art grain loss monitors have a detector transducer with a low resonant frequency while that one prior art grain loss monitor has a detector transducer with a resonant frequency of more than 100 KHz. In any event, none of the prior art monitors has a detector transducer and a conditioning circuitry which are tuned to each other.

It also will be seen from the above comparison that only the monitor according to the invention is capable of adequately to distinguish between dry grain and straw impact signals; the ratio of the detection rates of grain-to-straw in the given circumstances being in the range of 7.5. The prior art arrangement which comes closest to this ratio is the grain loss monitor C with a ratio in the range of 2.4 only. Several prior art grain loss monitors even have a grain-to-straw detection ratio of less than 1, which obviously is not at all acceptable.

The foregoing comparison further also indicates that also in wet crop conditions, the grain loss monitor according to the present invention is the only monitor capable adequately to distinguish between grain kernal and straw impacts; the ratio of the detection rates of grain-to-straw in the given circumstances still being in the range of 6.5 while that for the other grain loss monitors these ratios are situated around 0.7-0.8 (three times) and 2.1 (once). It should be kept in mind that these comparisons indeed have been made without any resetting of the monitors. This thus implies that with the monitor according to the invention there is no need to readjust the setting when the crop conditions vary from dry to wet.

Considering the findings with monitor D, i.e. the only monitor with a crystal detector having a resonant frequency of over 100 KHz, it will be noticed that the grain detection rate very substantially drops when the grain condition changes from dry to wet. In other words, the monitor D is very sensitive for variations in the humidity content of the grain kernals. It has indeed been found that wet wheat kernals produce signals which peak at a lower frequency level than dry wheat kernals. This may be one of the reasons for the substantial drop in the detection rates of the monitor D. It also has been found that the resonant frequency of the crystal detector and the frequency of the conditioning circuit associated therewith should not exceed 25 KHz to avoid the afore described problem of wet wheat kernal impacts not being detected adequately.

The foregoing comparison also indicates that the detection rates per se are not very important as such in as much as when low detection rates are obtained, an adequate signal nevertheless still can be derived therefrom by varying the sensitivity setting which, as already said, is the only adjustment possibility which has been maintained. The more important aspect is that the ratio of grain-to-straw impacts is high and remains high in all conditions. It thus can be stated in general that, with its ratio of detection rates of grain-to-straw well in excess of 4 under most or all circumstances, the monitor according to the invention constitutes a substantial progress in the art.

The present invention also represents an advance in the art in terms of the ease of control which the operator has to exercise in using the grain loss monitor. This is because he no longer has to make any judgement as between the type of crop being harvested and the moisture content thereof. All he needs to control is the gain at the output of the system in order to obtain a sensible level of signal which is truely indicative of the grain losses actually occurring at the rear of the machine. Also, the need to employ only a single transducer irrespective of the width (length) of the detector plate reduces manufacturing costs.

Reference has been made to the provision of two channels for the grain loss monitor but it will be appreciated that eventually only one channel may be employed, e.g. in association with the harvester separating mechanism, if the operator so desires. It further also will be appreciated that alternatively, further channels also can be employed if more than two detection points are required.

On the basis of two channels, however, the output of the respective integrators 23 are averaged using two resistors 29 and 30, with the averaged signals being applied to a third comparator 31 having a fixed threshold device 32 associated therewith. The comparator 31 compares the averaged signals from the integrators 23 with the fixed threshold to see whether it is greater or less than the latter. If an averaged signal is greater than the threshold, then the comparator 31 produces an output signal which is fed to an amplifier 33 and thence to an alarm device which may be in the form of one or more lamps 34 and/or an audio alarm (not shown). With this arrangement, the operator is warned whenever the gain loss signal from one or both of the channels 14 and 15 is relatively high. The threshold for the comparator 31 is set such that, if the signal from one channel is relatively high and the other relatively low, the alarm will be operated. Also, if the signals from both channels are such that they are within an essentially acceptable range, the alarm is still energised because the average is still considered high even though each signal per se is considered acceptable.

While the preferred structure, in which the principles of the present invention have been incorporated, is described above and is shown in the accompanying drawings, it is to be understood that the invention is not to be limited to the particular details as described above and shown in said drawings, but that, in fact, widely different means may be employed in the practice of the broader aspects of the invention.

The present invention may be employed to advantage in the grain loss measurement system of co-pending U.S. patent application Ser. No. 335,658, filed concurrently herewith and entitled "Method and Apparatus for Measuring Grain Loss in Harvesting Machines."

Having thus described the invention, what is claimed is:

1. A grain loss monitor for a harvesting machine operable to harvest crop material by separating grain kernels from debris contained in said crop material, comprising:
    detector means for detecting a loss of grain from said harvesting machine and including a sensor plate and transducer means operably connected to said sensor plate, said detector means being disposed for engagement with said crop material such that said sensor plate can register impacts of said grain kernels which cause a first high frequency vibration and the impact of said debris which causes a second low frequency vibration, said transducer means having a resonant frequency in the range of 8 to 25 KHz and is operable to convert physical vibrations from said sensor plate caused by the impacts of said grain kernels and said debris into electrical output signals having a dominate frequency corresponding to said resonant frequency, said resonant frequency being selected such that said first high frequency vibration effects a response of said transducer means more than said second low frequency vibration; and
    circuit means operable to process said electrical output signals from the transducer means and utilize said dominate resonant frequency to indicate the amount of grain kernels striking said sensor plate and thereby express an indication of grain loss from said harvesting machine.

2. The monitor of claim 1 wherein the resonant frequency of the transducer means is in the frequency range of 12 to 25 KHz.

3. The monitor of claim 2 wherein the resonant frequency of the transducer means is approximately 15 KHz.

4. The monitor of claim 3 wherein the transducer means consists of a single ceramic crystal transducer.

5. The monitor of claim 2 wherein the transducer means consists of a pair of ceramic crystal transducers having resonant frequencies which are situated generally at or adjacent opposite ends of said frequency range of 12 to 25 KHz.

6. The monitor of claim 1 wherein the circuit means has a frequency domain that is tuned to the resonant frequency of the transducer means.

7. The monitor of claim 6 wherein the circuit means comprises a high pass filter to which the output of the transducer means is connected.

8. The monitor of claim 7 wherein the high pass filter is of at least the sixth order.

9. The monitor of claim 8 wherein the high pass filter has a steep gradient in the frequency range of 10 to 15 KHz.

10. The monitor of claim 9 wherein the high pass filter is tuned to the frequency range of wave fronts of said output signals induced in the transducer means by grain kernel impacts on the sensor plate of the detector means.

11. The monitor of claim 10 wherein the circuit means comprises:
    a comparator having a threshold device with a set value associated therewith, said comparator being connected to the transducer means via the high pass filter to receive the output therefrom and to compare said high pass filter output with a set value in said threshold device; and
    an integrator provided with an adjustable gain control device, the output of the integrator being applied to an indicator means for displaying said integrator output.

12. The monitor of claim 11 wherein the set value in said threshold device associated with the comparator is adjustable.

13. The monitor of claim 12 wherein the high pass filter together with the comparator and the threshold device associated therewith form a signal conditioning circuit, said signal conditioning circuit being provided in the immediate vicinity of the transducer means, the circuit means also includes a second comparator to which the integrator is coupled and which also has a threshold device associated therewith, said second comparator and associated threshold device, said integrator, and gain control device and said indicator means together forming an indicator circuit which is provided at a remote location from the signal conditioning circuit and which is coupled thereto by a long lead to receive the signals therefrom.

14. The monitor of claim 13 wherein the indicator means comprise a bank of light emitting diodes, the number of diodes energized by the output of the integrator being adjustable by the adjustable gain control device associated with the integrator.

15. The monitor of claim 13 wherein the indicator means comprise a meter having a needle energized by the output of the integrator, and the position of said needle being adjustable by the adjustable gain control device associated with the integrator.

16. The monitor of claim 13 wherein the adjustable gain control device associated with the integrator is the only control to be operated by the operator for setting the monitor.

17. The monitor of claim 16 further comprising a plurality of channels, each channel having said detector means and said circuit means.

18. The monitor of claim 17 wherein two channels are provided, the output signals from the respective integrators of these two channels being averaged and the averaged signals being applied to a third comparator having a threshold device associated therewith; said monitor further comprising alarm means which are energized whenever the output signal from the third comparator exceeds the threshold set by the threshold device.

19. A grain loss monitor for a harvesting machine operable to harvest crop material by separating grain kernels from debris containing in said crop material, comprising:
    detector means for detecting a loss of grain from said harvesting machine and including a sensor plate and transducer means associated with said sensor plate, said detector means being engagable with said crop material such that said sensor plate can register impacts of said grain kernels which vibrate said sensor plate at a first high frequency and an impact of said debris which vibrates said sensor plate at a second low frequency, said transducer means having a resonant frequency such that said first high frequency vibration effects a greater resonance of said transducer means than said second low frequency vibration and is operable to convert physical vibrations from said sensor plate caused by the impacts of said grain kernels and said debris into electrical output signals having a dominate frequency corresponding to said resonant frequency; and circuit means operable to process said electrical output signals from the transducer means to indicate the amount of grain kernels striking said sensor plate and thereby express an indication of grain loss from said harvesting machine.

20. The monitor of claim 19 wherein said circuit means has a frequency domain tuned to said resonant frequency.

21. The monitor of claim 20 wherein said circuit means includes a high pass filter operable to enhance said dominant resonant frequency of said electrical output signals.

22. The monitor of claim 21 wherein said resonant frequency is in the resonant frequency range of 8 to 25 KHz.

23. The monitor of claim 22 wherein said transducer means includes a pair of ceramic crystal transducers having respective resonant frequencies at opposing ends of said resonant frequency range.

24. The monitor of claim 22 wherein said transducer means is in the form of a single ceramic crystal transducer having a resonant frequency at approximately 15 KHz.

25. A grain loss monitor for a harvesting machine operable to harvest crop material by separating grain kernels from debris contained in said crop material, comprising:

detector means for detecting a loss of grain from said harvesting machine and including a sensor plate and transducer means associated with said sensor plate, said detector means being engagable with said crop material such that said sensor plate can register impacts of said grain kernels which vibrate said sensor plate at a first high frequency and an impact of said debris which vibrates said sensor plate at a second low frequency, said transducer means having a resonant frequency such that said first high frequency vibration effects a greater resonance of said transducer means than said second low frequency vibration and is operable to convert physical vibrations from said sensor plate caused by the impacts of said grain kernels and said debris into electrical output signals in which said resonant frequency dominates; and circuit means having a frequency domain tuned to said resonant frequency and being operable to process said electrical output signals from the transducer means to indicate the amount of grain kernels striking said sensor plate and thereby express an indication of grain loss from said harvesting machine.

* * * * *